(12) United States Patent
Sico

(10) Patent No.: US 6,659,102 B1
(45) Date of Patent: Dec. 9, 2003

(54) OXYGEN MASK FILTER SYSTEM

(76) Inventor: Anthony L. Sico, 114 Moonlight Ct., Monroeville, PA (US) 15146

( * ) Notice: Subject to any disclaimer, the term of this patent is extended or adjusted under 35 U.S.C. 154(b) by 0 days.

(21) Appl. No.: 10/205,249

(22) Filed: Jul. 23, 2002

(51) Int. Cl.[7] .................. A62B 18/08; A62B 23/02; A62B 7/10

(52) U.S. Cl. ............... 128/206.15; 128/205.29; 128/206.12; 128/206.17; 128/205.25; 128/206.21; 128/206.28; 128/201.22; 128/205.27

(58) Field of Search ............. 128/205.12, 205.27, 128/205.29, 206.15, 206.17, 205.25, 206.21, 206.28, 201.22, 201.28, 206.12

(56) References Cited

U.S. PATENT DOCUMENTS

| | | | |
|---|---|---|---|
| 4,573,464 A | 3/1986 | Yo | 128/206.15 |
| 4,771,771 A | 9/1988 | Walther | 128/201.25 |
| 4,886,058 A | 12/1989 | Brostrom et al. | 128/206.12 |
| 4,963,327 A | 10/1990 | Russell | 422/120 |
| 5,036,844 A | 8/1991 | Pouchot et al. | 128/206.17 |
| 5,080,094 A | 1/1992 | Tayebi | 128/205.29 |
| 5,315,987 A | 5/1994 | Swann | 128/201.28 |
| 5,524,616 A | 6/1996 | Smith et al. | 128/205.27 |
| 5,579,761 A | 12/1996 | Yuschak et al. | 128/206.17 |
| 5,640,952 A | 6/1997 | Swann et al. | 128/206.17 |
| 5,996,580 A | 12/1999 | Swann | 128/206.17 |
| 6,216,693 B1 | 4/2001 | Rekow et al. | 128/205.27 |

Primary Examiner—Glenn K. Dawson
Assistant Examiner—Mark Rademacher

(57) ABSTRACT

An oxygen mask filter system for preventing the transmission of a disease from a patient to medical personnel. The oxygen mask filter system includes a face mask having an interior surface and an exterior surface, a plurality of vent apertures, a disk member movably attached to the exterior surface of the face mask about the vent apertures, and a filter member attached to the interior surface of the face mask for filtering gases prior to expulsion from the interior of the face mask to the exterior through the vent apertures.

14 Claims, 6 Drawing Sheets

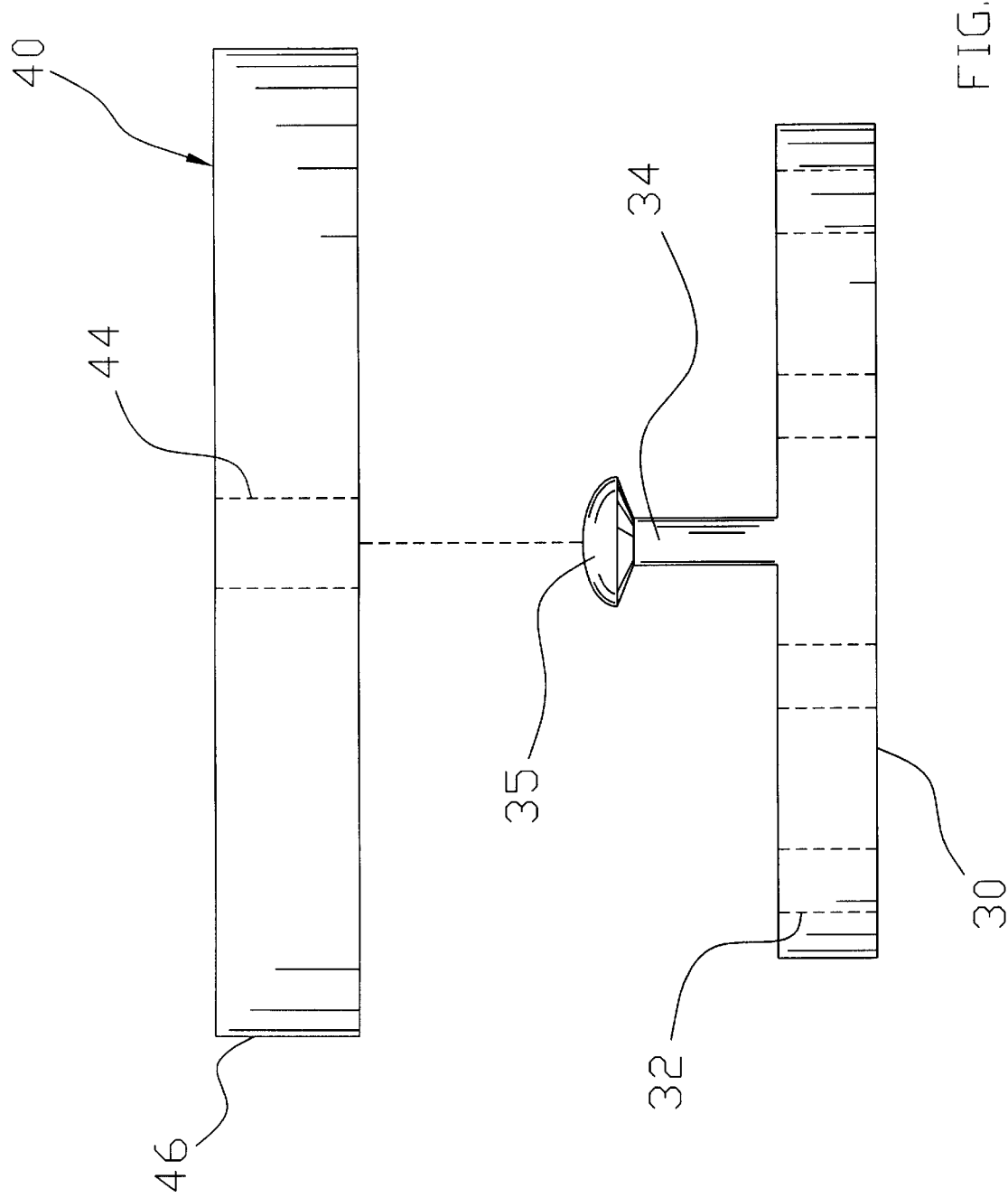

OXYGEN MASK FILTER SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to oxygen masks and more specifically it relates to an oxygen mask filter system for preventing the transmission of a disease from a patient to medical personnel.

2. Description of the Related Art

Oxygen masks have been in use for years. A conventional oxygen mask is comprised of a face mask that seals about the patient's mouth and nose, a check valve fluidly connected to the face mask, an oxygen bag fluidly connected to the check valve, and a pressurized oxygen tank fluidly connected to the oxygen bag as shown in FIG. 1 of the drawings. The face mask typically includes one or more vents within the side portions thereof wherein a disk member is loosely attached to a post member for allowing gases from within the face mask to be freely forced out of while preventing external gases from entering the interior of the face mask (i.e. similar to a check valve structure). The main problem with conventional oxygen masks is that they allow infectious diseases and organisms from the patient to be expelled from the face mask through the vents when the patient exhales.

Examples of patented devices which may be related to the present invention include U.S. Pat. No. 5,080,094 to Tayebi; U.S. Pat. No. 4,573,464 to Yo; U.S. Pat. No. 5,315,987 to Swann; U.S. Pat. No. 5,579,761 to Yuschak et al.; U.S. Pat. No. 6,216,693 to Rekow et al.; U.S. Pat. No. 5,996,580 to Swann; U.S. Pat. No. 5,640,952 to Swann et al.; U.S. Pat. No. 5,524,616 to Smith et al.; U.S. Pat. No. 5,036,844 to Pouchot et al.; U.S. Pat. No. 4,963,327 to Russell; U.S. Pat. No. 4,886,058 to Brostrom et al.; and U.S. Pat. No. 4,771,771 to Walther.

While these devices may be suitable for the particular purpose to which they address, they are not as suitable for preventing the transmission of a disease from a patient to medical personnel. Conventional oxygen masks do not protect medical personal from infectious diseases and organisms expelled from a patient.

In these respects, the oxygen mask filter system according to the present invention substantially departs from the conventional concepts and designs of the prior art, and in so doing provides an apparatus primarily developed for the purpose of preventing the transmission of a disease from a patient to medical personnel.

SUMMARY OF THE INVENTION

In view of the foregoing disadvantages inherent in the known types of oxygen masks now present in the prior art, the present invention provides a new oxygen mask filter system construction wherein the same can be utilized for preventing the transmission of a disease from a patient to medical personnel.

The general purpose of the present invention, which will be described subsequently in greater detail, is to provide a new oxygen mask filter system that has many of the advantages of the oxygen masks mentioned heretofore and many novel features that result in a new oxygen mask filter system which is not anticipated, rendered obvious, suggested, or even implied by any of the prior art oxygen masks, either alone or in any combination thereof.

To attain this, the present invention generally comprises a face mask having an interior surface and an exterior surface, a plurality of vent apertures, a disk member movably attached to the exterior surface of the face mask about the vent apertures, and a filter member attached to the interior surface of the face mask for filtering gases prior to expulsion from the interior of the face mask to the exterior through the vent apertures.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide an oxygen mask filter system that will overcome the shortcomings of the prior art devices.

A second object is to provide an oxygen mask filter system for preventing the transmission of a disease from a patient to medical personnel.

Another object is to provide an oxygen mask filter system that filters gases from the interior of the face mask prior to being expelled.

An additional object is to provide an oxygen mask filter system that allows for the filters to be conveniently removed or changed.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 6 is a side view of the filter device.

DETAILED DESCRIPTION OF THE INVENTION

Figure 1:
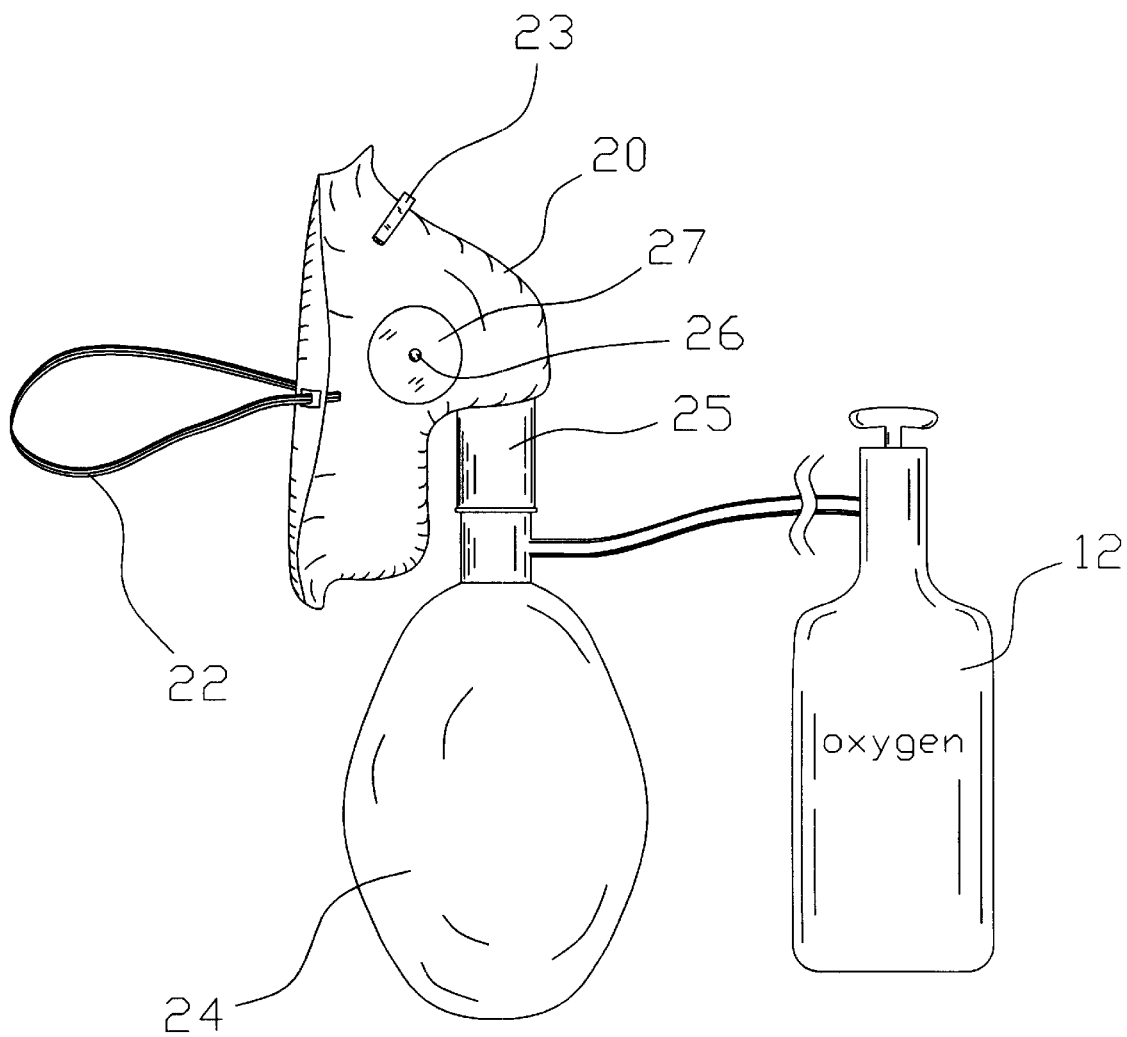
FIG. 1 is a side view of a prior art oxygen mask system.

Turning now descriptively to the drawings, in which similar reference characters denote similar elements throughout the several views, FIGS. 2 through 6 illustrate an oxygen mask filter system 10, which comprises a face mask 20 having an interior surface and an exterior surface, a plurality of vent apertures 28, a disk member 27 movably attached to the exterior surface of the face mask 20 about the vent apertures 28, and a filter member 40 attached to the interior surface of the face mask 20 for filtering gases prior to expulsion from the interior of the face mask 20 to the exterior through the vent apertures 28.

FIG. 1 illustrates a prior art oxygen mask system. A conventional oxygen mask is comprised of a face mask 20 that seals about the patient's mouth and nose, a check valve 25 fluidly connected to the face mask 20, an oxygen bag 24 fluidly connected to the check valve 25, and a pressurized oxygen tank 12 fluidly connected to the oxygen bag 24 as shown in FIG. 1 of the drawings. The face mask 20 typically includes one or more vents within the side portions thereof wherein a disk member 27 is loosely attached to an outer post 26 for allowing gases from within the face mask 20 to be freely forced out of while preventing external gases from entering the interior of the face mask 20. The face mask 20 further typically has at least one securing strap 22 and a band member 23 for forming the shape of the face mask 20.

Figure 2:
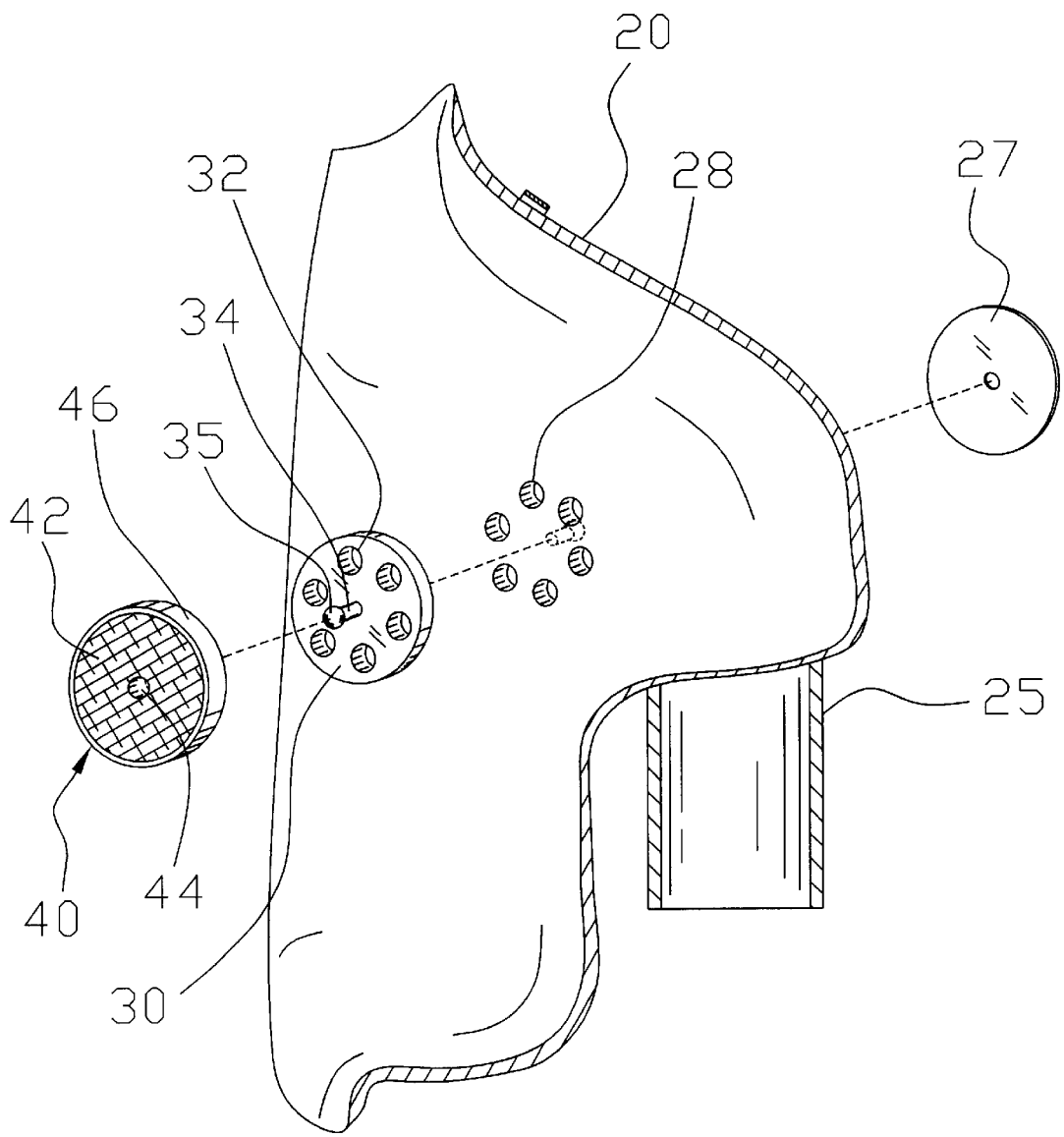
FIG. 2 is an exploded side cutaway view of the present invention.
Figure 3:
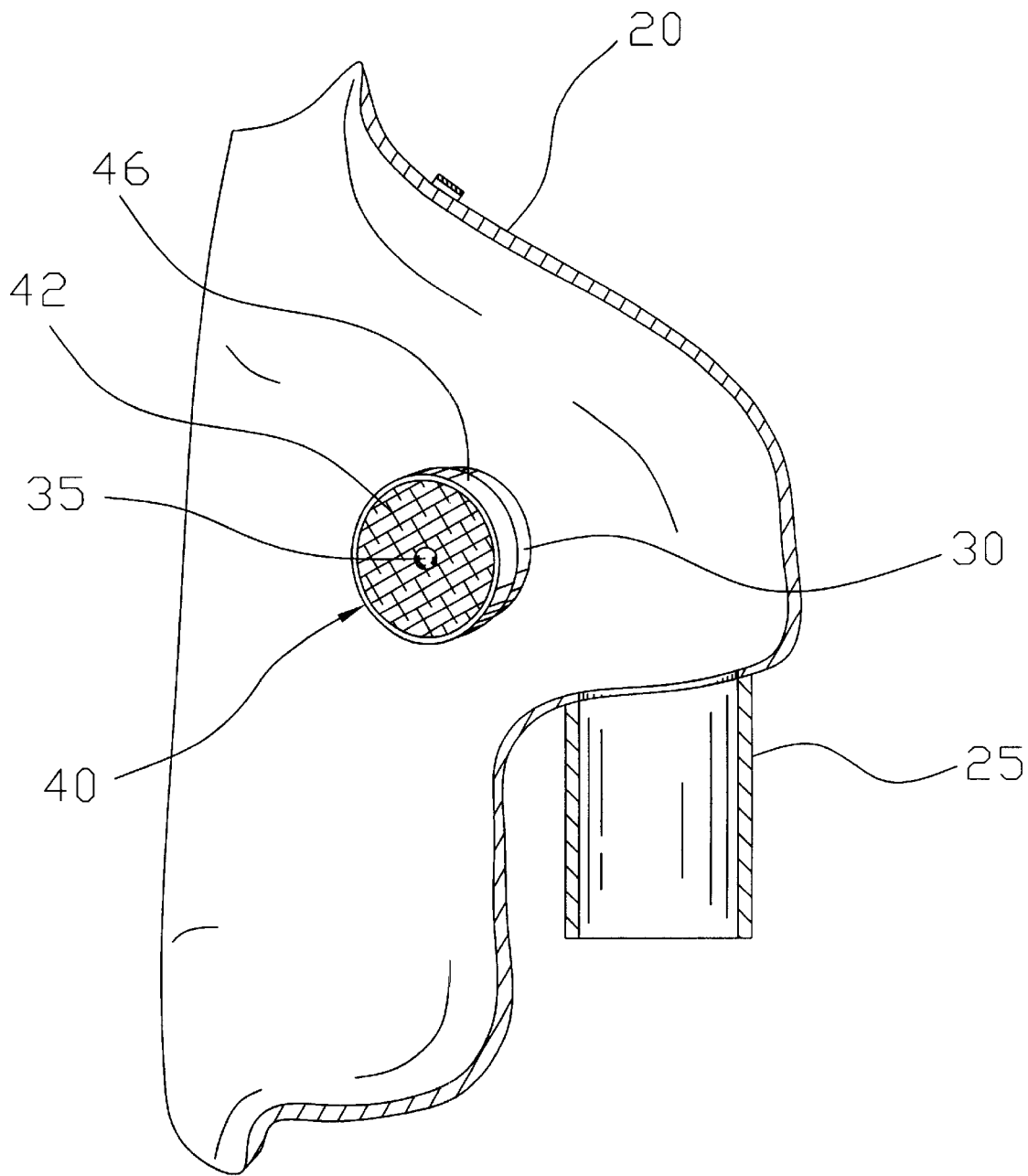
FIG. 3 is a side cutaway view of the present invention.
Figure 4:
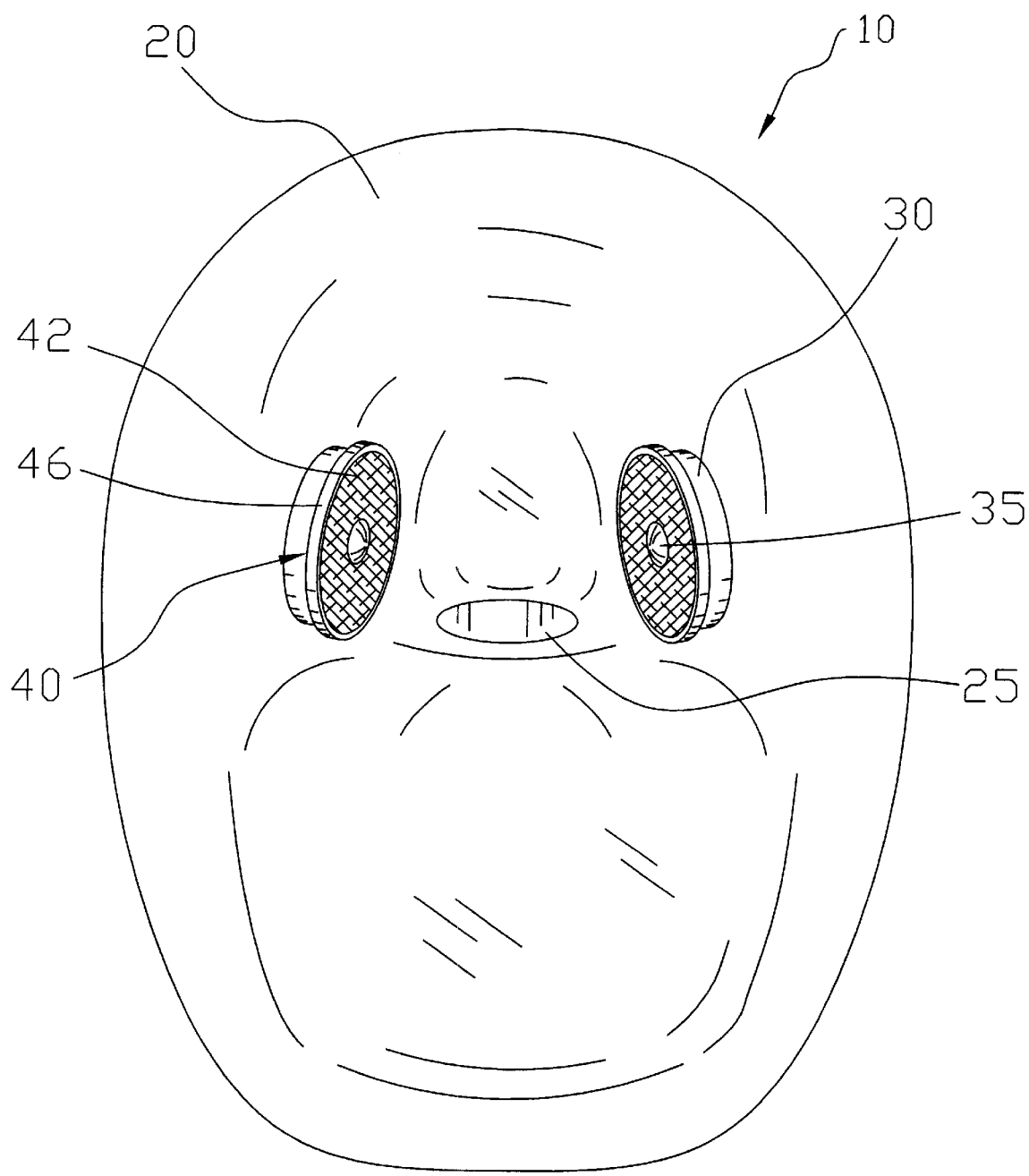
FIG. 4 is a rear view of the present invention.
Figure 5:
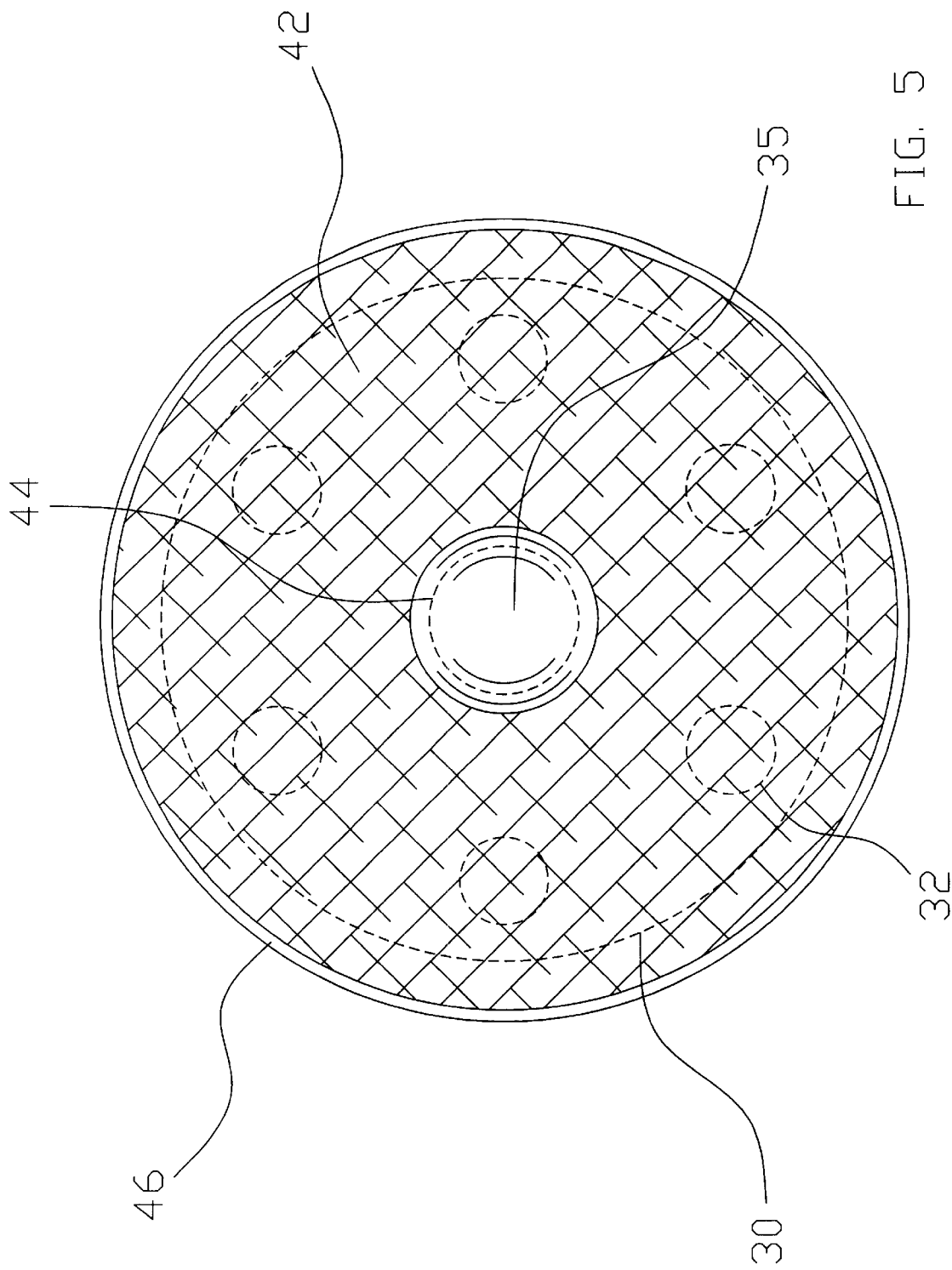
FIG. 5 is an interior view of the filter device.

As shown in FIGS. 2 through 4 of the drawings, the face mask 20 is formed to fit snugly in a sealed manner about the patient's face. The face mask 20 may have various other shapes and structures other than that illustrated in the figures as can be appreciated by one skilled in the art. The face mask 20 may be constructed of various materials such as but not limited to plastic.

As best shown in FIG. 2, the face mask 20 preferably has at least one set of a plurality of vent apertures 28 within that allow gases from within the interior cavity of the face mask 20 to escape through when the patient exhales. The plurality of vent apertures 28 may form various designs and patterns, however conventional oxygen masks typically have a circular structure as illustrated in FIG. 2 of the drawings. The vent apertures 28 may have various sizes and shapes which allow adequate gas flow through thereof.

On the exterior surface of the face mask 20, a disk member 27 is movably attached about an outer post 26 positioned adjacent the vent apertures 28. The disk member 27 is preferably comprised of a material capable of sealing the vent apertures 28 when the patient inhales such as but not limited to rubber or plastic. The disk member 27 may have various sizes and shapes which are well-known in the medical industry.

Within the interior of the face mask 20, an inner post 34 extends inwardly from the interior surface of the face mask 20 for supporting the filter member 40. The inner post 34 preferably is positioned adjacent to the vent apertures 28 and more particularly. centrally within the vent apertures 28. A plate member 30 may be attached to the interior surface about the vent apertures 28 wherein the plate member 30 has a number of plate apertures 32 within that correspond to the vent apertures 28 as best illustrated in FIG. 2 of the drawings.

As shown in FIGS. 2 and 6 of the drawings, the inner post 34 preferably has a flanged end 35 for snugly retaining the filter member 40 upon the inner post 34. The flanged end 35 preferably is formed for allowing the filter member 40 to be easily attached and more difficult to remove from the inner post 34 as best illustrated in FIG. 6 of the drawings.

As shown in FIGS. 2 through 5 of the drawings, the filter member 40 has a filter element 42 capable of filtering micro-particulate material, microorganisms, saliva, airborne diseases and other health hazard materials. The filter element 42 may be comprised of various materials commonly utilized within the medical industry for filtering air-borne diseases.

As shown in FIGS. 2 and 6 of the drawings, a filter aperture 44 extends through the filter element 42 for fitting about the inner post 34. The filter aperture 44 may have various shapes and sizes that are suitable for easy positioning about the flanged end 35 of the inner post 34. The filter aperture 44 is preferably centrally positioned within the filter element 42, however the filter aperture 44 may be positioned within various other locations within the filter element 42. The filter member 40 preferably includes an outer encasement 46 for providing increased rigidity to the filter element 42 and for preventing the passing of material through the side portions of the filter element 42.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:
1. An oxygen mask filter system, comprising:
a face mask having a plurality of vent apertures;
a disk member movably attached to an exterior surface of said face mask for selectively closing said plurality of vent apertures when a patient inhales and opening said plurality of vent apertures when a patient exhales;
a plate member attached to an interior surface of said face mask, said plate member having a plurality of plate apertures corresponding to said vent apertures;
an inner post extending from said plate member; and
a filter member removably attached to said inner post positioned about said plurality of vent apertures for filtering gases escaping from said face mask through said plurality of vent apertures.
2. The oxygen mask filter system of claim 1, wherein said filter member is capable of filtering micro-particulate material.
3. The oxygen mask filter system of claim 1, wherein said filter member is comprised of a filter element and an outer encasement surrounding a perimeter of said filter element.

4. The oxygen mask filter system of claim 1, wherein said filter member has a circular structure.

5. The oxygen mask filter system of claim 1, including an outer post extending from said exterior surface of said face mask adjacent said plurality of vent apertures thereby movably supporting said disk member.

6. The oxygen mask filter system of claim 1, wherein said inner post has a flanged end for retaining said filter member upon thereof.

7. The oxygen mask filter system of claim 1, wherein said filter member has a filter aperture that is formed to fit about said inner post.

8. An oxygen mask filter system, comprising:

a face mask having a plurality of vent apertures;

a disk member movably attached to an exterior surface of said face mask for selectively closing said plurality of vent apertures when a patient inhales and opening said plurality of vent apertures when a patient exhales;

a plate member attached to an interior surface of said face mask, said plate member having a plurality of plate apertures corresponding to said vent apertures;

an inner post extending from said plate member; and a filter member attached to said inner post positioned about said plurality of vent apertures.

9. The oxygen mask filter system of claim 8, wherein said filter member is capable of filtering micro-particulate material.

10. The oxygen mask filter system of claim 8, wherein said filter member is comprised of a filter element and an outer encasement surrounding a perimeter of said filter element.

11. The oxygen mask filter system of claim 8, wherein said filter member has a circular structure.

12. The oxygen mask filter system of claim 8, including an outer post extending from said exterior surface of said face mask adjacent said plurality of vent apertures thereby movably supporting said disk member.

13. The oxygen mask filter system of claim 8, wherein said inner post has a flanged end for retaining said filter member upon thereof.

14. The oxygen mask filter system of claim 8, wherein said filter member has a filter aperture that is formed to fit about said inner post.

* * * * *